United States Patent
Ji et al.

(10) Patent No.: US 10,743,781 B2
(45) Date of Patent: Aug. 18, 2020

(54) ISCHEMIC PRECONDITION TREATMENT EQUIPMENT AND USE AND METHOD THEREOF FOR JUDGING HEALTH CONDITION OF BLOOD VESSELS

(71) Applicant: Xunming Ji, Beijing (CN)

(72) Inventors: Xunming Ji, Beijing (CN); Qianrui Chen, Beijing (CN)

(73) Assignee: Xunming Ji, Beijing (CN)

( * ) Notice: Subject to any disclaimer, the term of this patent is extended or adjusted under 35 U.S.C. 154(b) by 363 days.

(21) Appl. No.: 15/539,956

(22) PCT Filed: Jan. 15, 2015

(86) PCT No.: PCT/CN2015/070731
§ 371 (c)(1),
(2) Date: Jun. 26, 2017

(87) PCT Pub. No.: WO2016/101367
PCT Pub. Date: Jun. 30, 2016

(65) Prior Publication Data
US 2017/0347897 A1 Dec. 7, 2017

(30) Foreign Application Priority Data

Dec. 26, 2014 (CN) .......................... 2014 1 0834305

(51) Int. Cl.
*A61B 5/022* (2006.01)
*A61B 5/021* (2006.01)
(Continued)

(52) U.S. Cl.
CPC ........ *A61B 5/0225* (2013.01); *A61B 5/02007* (2013.01); *A61B 5/0235* (2013.01);
(Continued)

(58) Field of Classification Search
CPC ........... A61B 5/02; A61B 5/021; A61B 5/022; A61B 5/0225; A61B 5/02007;
(Continued)

(56) References Cited

U.S. PATENT DOCUMENTS 4,718,426 A    1/1988   Russell
5,050,613 A    9/1991   Newman et al.
(Continued)

FOREIGN PATENT DOCUMENTS

CN    201098315 Y    8/2008
CN    101317805 A    12/2008
(Continued)

OTHER PUBLICATIONS

Fibocom, "G510 Hardware User Manual", Nov. 26, 2013, https://www.tme.eu/Document/fabb43e22a46fba821931db19e577988/FIBOCOM_G510_U_M.pdf, Jun. 25, 2019 (Year: 2013).*
(Continued)

*Primary Examiner* — Etsub D Berhanu
*Assistant Examiner* — James Stewart Stambaugh, III
(74) *Attorney, Agent, or Firm* — Leydig, Voit & Mayer, Ltd.

(57) ABSTRACT

Disclosed is ischemic precondition treatment equipment and a use and method thereof for judging health condition of blood vessels. A gas way structure (4) is arranged inside a shell of ischemic precondition training treatment equipment. The gas way structure comprises a 5-way device (43). The 5-way device (43) is connected to a left gas pump (41), a right gas pump (42), a left solenoid valve (44), a right solenoid valve (45) and a release valve (48), respectively. The gas way structure (4) can rapidly bring a pressure of an armband airbag to the set pressure value in a short period of time, which is effective in relieving the patients' discomfort and pain when used. It is suitable for long-term use for
(Continued)

training. In addition, it also can judge the health condition of blood vessels.

3 Claims, 2 Drawing Sheets

(51) Int. Cl.
    *A61B 5/0225* (2006.01)
    *A61B 5/02* (2006.01)
    *A61B 5/0235* (2006.01)
    *A61H 9/00* (2006.01)
    *A61B 5/00* (2006.01)

(52) U.S. Cl.
    CPC ....... *A61B 5/02225* (2013.01); *A61H 9/0092* (2013.01); *A61B 5/742* (2013.01); *A61B 2505/09* (2013.01)

(58) Field of Classification Search
    CPC ... A61B 5/02225; A61B 5/0235; A61B 5/742; A61B 5/74
    See application file for complete search history.

(56) References Cited

U.S. PATENT DOCUMENTS

| | | | | |
|---|---|---|---|---|
| 2004/0171940 | A1* | 9/2004 | Narimatsu | A61B 5/021 600/485 |
| 2009/0018422 | A1* | 1/2009 | Banet | A61B 5/02007 600/324 |
| 2010/0234742 | A1* | 9/2010 | Lin | A61B 5/022 600/490 |
| 2011/0238107 | A1 | 9/2011 | Raheman | |
| 2012/0065561 | A1* | 3/2012 | Ballas | A61H 9/0021 601/152 |
| 2013/0274621 | A1* | 10/2013 | Park | A61B 5/742 600/492 |
| 2014/0114117 | A1* | 4/2014 | Naghavi | A61B 5/02233 600/13 |
| 2014/0194755 | A1* | 7/2014 | Ide | A61B 5/6843 600/494 |
| 2014/0343441 | A1* | 11/2014 | Alatriste | A61B 5/021 600/485 |

FOREIGN PATENT DOCUMENTS

| | | |
|---|---|---|
| CN | 201316381 Y | 9/2009 |
| CN | 201631183 U | 11/2010 |
| CN | 202335859 U | 7/2012 |
| CN | 202505429 U | 10/2012 |
| CN | 102895013 A | 1/2013 |
| CN | 202801711 U | 3/2013 |
| CN | 203138608 U | 8/2013 |
| CN | 203139071 U | 8/2013 |
| CN | 103281955 A | 9/2013 |
| CN | 203169547 U | 9/2013 |
| CN | 203169547 U | 9/2013 |
| CN | 203263775 U | 11/2013 |
| CN | 203315307 U | 12/2013 |
| CN | 103584845 A | 2/2014 |
| CN | 204351819 U | 2/2014 |
| EP | 1785087 | 5/2007 |
| JP | 2009523512 A | 6/2009 |
| JP | 2012239513 A | 12/2012 |
| JP | 2014014556 A | 1/2014 |

OTHER PUBLICATIONS

Japanese Office Action, dated Nov. 1, 2018, in Japanese Patent Application No. 2017-552201, a related application, 2 pp.
European Search Report, dated Aug. 21, 2018, corresponding to European Application No. 15871446.9, a related application, 9 pp.
Clark et al. (2012) "Association of a difference in systolic blood pressure between arms with vascular disease and mortality: a systematic review and meta-analysis," Lancet. 379(9819):905-914.
International Search Report with Written Opinion corresponding to International Patent Application No. PCT/CN2015/070731, dated Sep. 22, 2015.

* cited by examiner

ISCHEMIC PRECONDITION TREATMENT EQUIPMENT AND USE AND METHOD THEREOF FOR JUDGING HEALTH CONDITION OF BLOOD VESSELS

CROSS-REFERENCE TO RELATED APPLICATIONS

This application is a U.S. National Stage Application filed under 35 U.S.C. § 371 of International Application No. PCT/CN2015/070731, filed Jan. 15, 2015, which claims the benefit of Chinese Application No. 201410834305.2, filed Dec. 26, 2014. Both of these applications are hereby incorporated by reference in their entireties.

TECHNICAL FIELD

The present invention relates to the technical field of prevention and treatment of cardio-cerebrovascular disease, in particular to an ischemic precondition treatment equipment and a use and method thereof for judging health condition of blood vessels.

BACKGROUND ART

The applicants of the present application, J I Xunming et al., filed applications entitled *Cerebrovascular and Cardiovascular Health Care and Therapeutic Equipment* in 2007 (with the application numbers of 200720173945.9 and 200710176701.0). In 2011, the applicant, upon applying for a category classification for such equipment before China Food and Drug Administration, named the equipment for said purpose as "ischemic precondition training treatment equipment", and the name was adopted by China Food and Drug Administration. Subsequently, products of this category are all entitled "ischemic precondition training treatment equipment" for application, registration or commercial purpose. Nevertheless, after long-term clinical application and patient tracking service, some problems still exist in the known ischemic precondition training. These problems are not totally solved by the prior patent documents and products, which are illustrated as follows:

CN202335859U discloses a remote ischemic preconditioning equipment, which adopts the technical solution of adding a device to the main body of electronic sphygmomanometer, in which the device could inflate and deflate the armlet multiple times in a repeated, continuous and timing way, so as to repeatedly and continually block the blood flow of the limbs in short time. CN 202505429U is realized by adding a sensing means for measuring the oxygen value of pulse on the basis of the equipment disclosed in CN202335859U, in which the equipment is continuously pressurized 200 mmHg until the oxygen value of pulse cannot be measured, then the inflating pump ceased to work, and the pressure value is that set for blocking blood flow. Since the oxygen value of pulse refers to the oxygen content measured according to the oxygen content in blood per every pulse in vessel, the value measured in accordance with said method, in practical use, is admitted under the circumstances that the arm is under normal condition, i.e. the arm is not pressed and the blood vessel is not blocked. When the armlet begins to inflate, it presses the arm and the blood is blocked, and thus the oxygen value of pulse rapidly decreases to zero. Under such condition, the pressure value in armlet is not certain. Even another 200 mgHg pressure is added to the uncertain pressure value (as basis), the pressure required for preconditioning training is still not satisfied, which would incur swelling pain in practice.

Patent documents CN203263775U and CN203315307U disclose that "by adopting said structure, the present utility model is concluded through multiple repeated experiments to have the advantages of promoting the patients' blood circulation by pressing repeatedly to relax the upper and lower limbs, in such a way to produce stress reaction as a result of the blocked limbs being ischemic stimulated instantly". Such design cannot satisfy the requirements for preconditioning training method, i.e. the requirements for blocking vessels of upper limbs rapidly. The reason is that, during the process of inflating and applying pressure to the airbag of the upper limbs in the preconditioning training, the pressure applied to arms would firstly block the superficial veins, i.e. blocking bloods to reflow to heart, while the deep arterial vessels are not blocked and would still deliver bloods to arms; if larger pressure cannot be applied rapidly, fingers would swell and extravasate, and thus the treatment equipment cannot be extruded repeatedly. As to the training on lower limbs by means of the airbag described in the patents, it can be clearly determined from the existing documents that the preconditioning training cannot be practiced on lower limbs, since such action would make thrombosis in lower limb venography to be an event of larger probability.

CN202801711U discloses a remote ischemic preconditioning training equipment, which comprises a first pressure sensor in the air pressure regulation portion for providing a real-time feedback of air pressure, and a second pressure sensor disposed in the contact part between the armlet and the user for measuring the real-time pressure of the armlet on user's arm. Said equipment is to train users by applying dynamic extrusion to user's arms. Such design is not directed to the key points of ischemic preconditioning training method, and may make the preconditioning treatment uncomfortable or potentially risky.

The applicants ZHENG Cai'er et al. and the associated enterprise successively applied a plurality of patents (CN203138608U, CN203139071U, CN102895013A and CN203169547U) for ischemic preconditioning treatment equipment. The patent documents describe that "Capital Medical University-Xuanwu Hospital adopts an in vitro safe physical non-invasive method, i.e. a distal ischemic precondition training method", for being used in ischemic precondition training. Moreover, the patents mentioned that "there is no study on medical apparatuses and equipment using said principle in the present industry, and how to fully utilize the principle to study the corresponding medical apparatus and equipment is a topic faced by those skilled in the art". In fact, Capital Medical University-Xuanwu Hospital, as the national pioneer search team in ischemic preconditioning training, has successively developed the preconditioning treatment equipment in the year of 2008. Moreover, the developed equipment is further studied and improved these years and has served thousands of patients. Nevertheless, the ischemic preconditioning treatment equipment in aforementioned patents have disadvantages in clinical application and structure, rendering the patients having discomfortableness of swelling and extravasated blood in fingers during preconditioning training owing to the unreasonable design regarding the internal gas way structure. Additionally, as to the equipment of said patent documents, there are imperfections in disposition of inflator pumps and patient experience, and no adjustments are made regarding the key points of the ischemic preconditioning training method. Thus, the equipment disclosed in said patent documents are merely for realizing the function of ischemic preconditioning treatment, but the ischemic preconditioning treatment object cannot be really achieved.

In conclusion, the existing distal ischemic preconditioning treatment equipment are mostly obtained through improvement on the known sphygmomanometer. It is true that the provided technical solutions could substantially accomplish said function according to the requirements for ischemic preconditioning training; however, the treatment effect of ischemic preconditioning treatment can be accomplished with the proviso that the patients insist on using it for at least three months, and the prevention object can only be achieved only if the users keep on training for a long term. Moreover, some equipment are modified to restrict the power of gas pump for achieving the accuracy of blood pressure measurement. Although such modified structures could make the equipment achieve preconditioning training function, they cannot accomplish effective preconditioning training, and further cannot produce excellent treatment effect.

At present, the diagnosis standard for inter-arm blood pressure difference (IAD) is that: if IAD≥10 mmHg, it will be deemed as abnormity. Some studies classify the systolic pressure IAD (sIAD) into two grades: the first grade of sIAD≥10 mmHg, and the second grade of sIAD≥20 mmHg. Moreover, the diastolic pressure IAD (dIAD) is ≥10 mmHg. If a patient has high IAD, it is reminded that the patient might have peripheral vascular disease.

The current research findings show that in 386 patients suspected to have coronary heart disease, 27 patients (7%) with sIAD ≥15 mmHg have larger myocardial ischemia area, 63% of the IAD patients are diagnosed to have coronary heart disease and 83% of them suffer from multi-vessel disease. Thus, IAD may be an indication for coronary artery lesions.

Currently, most foreign scholars use the name of inter-arm blood pressure difference (IAD). Now, it is generally deemed that the IAD of systolic pressure and diastolic pressure for normal people shall both be lower than 10 mmHg. There are two relevant studies in foreign countries at present. In one study, 83 patients were observed and followed-up for 5.6 year, which shows that the mean event-free survival of dIAD is 3.3 year, and that of non-dIAD is 5.0 years (P<0.0001). In the other study, 421 patients were observed and followed-up for 7 years. These two studies show that the cardio-cerebrovascular disease event in IAD patients increases. Having corrected the factors of mean systolic pressure and chronic nephrosis, it is found that for every 10 mmHg sIAD variation, the mortality risk ratio is 1.24 (95% credibility interval is 1.01-1.52). A prospective study in the United States shows that if the blood pressure disparity of two arms of a patient is ≥20/10 mmHg, the incidence and mortality of cardio-cerebrovascular disease would increase significantly.

Clark C E et al. published a paper in the famous medical journal Lancet, which, by analyzing the previous medical documents, determines that the risk of having cardio-cerebrovascular disease may be to some extend predicted according to the blood pressure disparity between two arms. Relevant study reports include 28 papers. According to the reports, there is evidence showing that if IAD reaches 10 mmHg, the patient may suffer from peripheral vascular disease; if the IAD is higher than 15 mmHg, the risk of having peripheral vascular disease (i.e. the vascular narrows and hardens) is high, and it may also shows that the person suffers from a pre-existing cerebrovascular disease. The reason is that the high IAD renders the risk of reduction in blood that flows to two legs and two feet being increased by 2.5-fold, the risk of reduction in blood that flows to the brain being increased by 1.6-fold, the risk of dying from cardiovascular disease being increased by 70%, and the risk of dying from other diseases being increased by 60%. If the health condition can be judged according to the measured IAD numerical value and the peripheral vascular disease (PVD) can be discovered earlier, the measures of reducing blood pressure and cholesterol and quitting smoking are helpful for reducing the risk of death.

SUMMARY OF THE INVENTION

The object of the present invention is to provide an ischemic precondition training treatment equipment, which has multiple functions including judgment of health condition of blood vessels, blood pressure measurement of both arms and ischemic precondition training, to address deficiencies in the prior art.

Another object of the present invention is the use and method of such ischemic precondition training treatment equipment for judging health condition of blood vessels.

In order to achieve the objects of the present invention, the technical solution adopted is as follows: ischemic precondition training treatment equipment, comprising a shell, armbands, buttons mounted on the shell, a display screen and a control circuit, characterized in that, the shell is provided with two armband plugholes for connecting the armbands on both left and right sides, respectively; a gas way structure is provided within the shell; the gas way structure comprises a 5-way device, which is connected to a left gas pump, a right gas pump, a left solenoid valve, a right solenoid valve and a release valve, respectively; the left solenoid valve is connected to a left armband holder, with a left pressure sensor provided therebetween; the right solenoid valve is connected to a right armband holder, with a right pressure sensor provided therebetween; the left armband holder and the right armband holder are connected with the armband plugholes on both sides of the shell, respectively.

The control circuit comprises a microprocessor, an A/D conversion chip, a clock/calendar chip, a memory chip, and a power supply circuit. The microprocessor is connected to a GPRS module.

Specifically, the GPRS module comprises a GPRS transceiver chip, a SIM card slot, a power amplification chip and an antenna. The GPRS transceiver chip is provided with an RxD port and a TxD port, and the GPRS transceiver chip is connected with the microprocessor through the RxD port and the TxD port. The GPRS transceiver chip is also connected with the SIM card slot and the power amplification chip, respectively, and the power amplification chip is connected with the antenna.

The GPRS transceiver chip is connected with a serial communications interface of the microprocessor by means of the RxD port and the TxD port, reads data from the memory chip, and sends the data back to a background server after the completion of training or blood pressure measurement each time. In order to avoid the loss of transceiving data, the data signals are amplified by the power amplification circuit and then are transmitted and received by the antenna, and data before the last shutdown is transmitted repeatedly upon each boot-up so as to perform comparison and verification.

Use of the aforesaid ischemic precondition training treatment equipment, characterized in that the ischemic precondition training treatment equipment is used for judging health condition of blood vessels.

A method of the aforesaid ischemic precondition training treatment equipment for judging health condition of blood vessels, comprising the following steps:

(1) wearing two armbands on left and right arms of a user respectively, and connecting plugholes of the two armbands with a left armband holder and a right armband holder respectively;

(2) starting the ischemic precondition training treatment equipment, which firstly pressurizes the left arm to begin the first blood pressure measurement, calculates systolic pressure, diastolic pressure and pulse measured from the left arm according to the principle of oscillography, and automatically memorizes and stores the result of the first measurement after the completion of measurement, wherein talking, motion and abnormality of the armbands during the measurement would result in an abnormal measurement result, the abnormal data would not be memorized, and the measurement will be restarted until an accurate measurement result is obtained;

(3) then automatically performing the first blood pressure measurement of the right arm, calculating systolic pressure, diastolic pressure and pulse measured from the left arm, and automatically memorizes and stores the result of the first measurement after the completion of measurement;

(4) after repeating three effective measurements, displaying the difference value of the average value of the systolic pressures and the difference value of the average value of the diastolic pressures measured between the left arm and the right arm on a screen; and (5) judging health condition of blood vessels according to the difference value measured from the step (4).

Research data shows that it is generally deemed that the difference value of systolic pressure and the difference value of diastolic pressure between both arms for a normal person shall both be smaller than 10 mmHg. If the upper inter-arm blood pressure difference (IAD) reaches 10 mmHg, the person might have peripheral vascular disease.

Compared with the prior art, the present invention has the following advantageous effects:

(1) the gas way structure of the present invention can rapidly bring the pressure of an armband airbag to a set pressure value in a short period of time, effectively relieving the patients' discomfort and pain when used, and thus is suitable for long-term use for training;

(2) the present invention not only achieves arbitrary switching of left and right arms to separately perform ischemic precondition training or simultaneous ischemic precondition training of both arms, which meets clinical requirements on ischemic precondition training, but also has a function of judging health condition of blood vessels; patients can judge their own condition of vascular health by the ischemic precondition treatment equipment provided by the present invention.

DETAILED DESCRIPTION OF EMBODIMENTS

The present invention is further described in details with reference to a specific example below. It should be understood that the specific example described herein is merely intended to explain the present invention without limitation.

EXAMPLE

Figure 1:
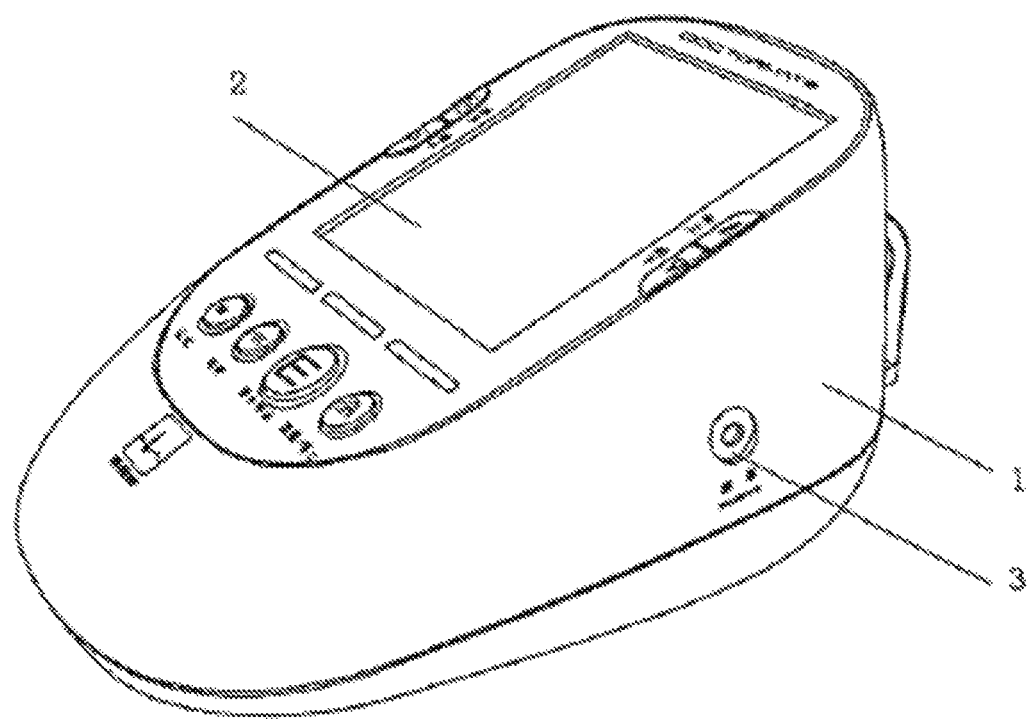
FIG. 1 illustrates a schematic diagram of the design structure of ischemic precondition training treatment equipment.

FIG. 1 shows an ischemic precondition training treatment equipment, comprising a shell 1, armbands, and buttons mounted on the shell, a display screen 2 and a control circuit. The shell 1 is provided with two armband plugholes 3 for connecting the armbands on both left and right sides, respectively.

Figure 2:
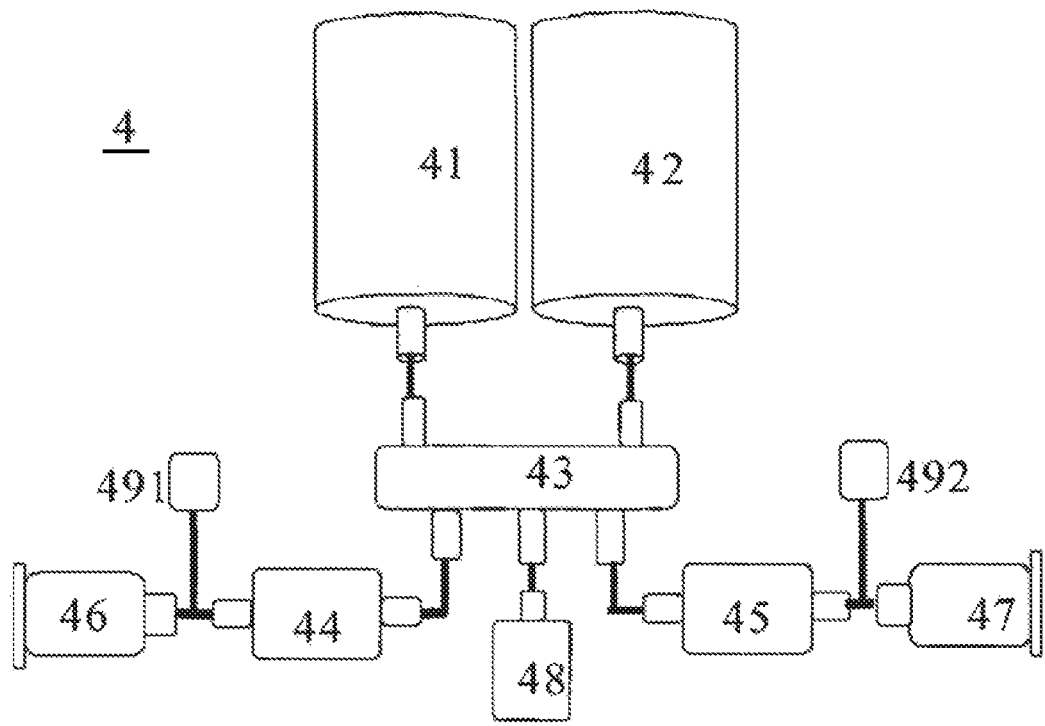
FIG. 2 illustrates a schematic diagram of a gas way structure of the ischemic precondition training treatment equipment.

A gas way structure 4 is provided within the shell 1, as shown in FIG. 2. The gas way structure 4 comprises a 5-way device 43, which is connected to a left gas pump 41, a right gas pump 42, a left solenoid valve 44, a right solenoid valve 45 and a release valve 48, respectively. The left solenoid valve 44 is connected to a left armband holder 46, with a left pressure sensor 491 provided therebetween. The right solenoid valve 45 is connected to a right armband holder 47, with a right pressure sensor 492 provided therebetween. The left armband holder 46 and the right armband holder 47 are connected with the armband plugholes 3 on both sides of the shell 1, respectively.

The aforesaid gas way structure can rapidly bring the pressure of an armband airbag to a set pressure value in a short period of time. Some known ischemic precondition treatment equipment in the prior art are mostly obtained by improvement on the basis of sphygmomanometer and even makes certain restrictions on the power of a gas pump in order to achieve accuracy for blood pressure measurements, as a result of which they cannot obtain an effective precondition training effect, though they have the precondition training function.

Figure 3:
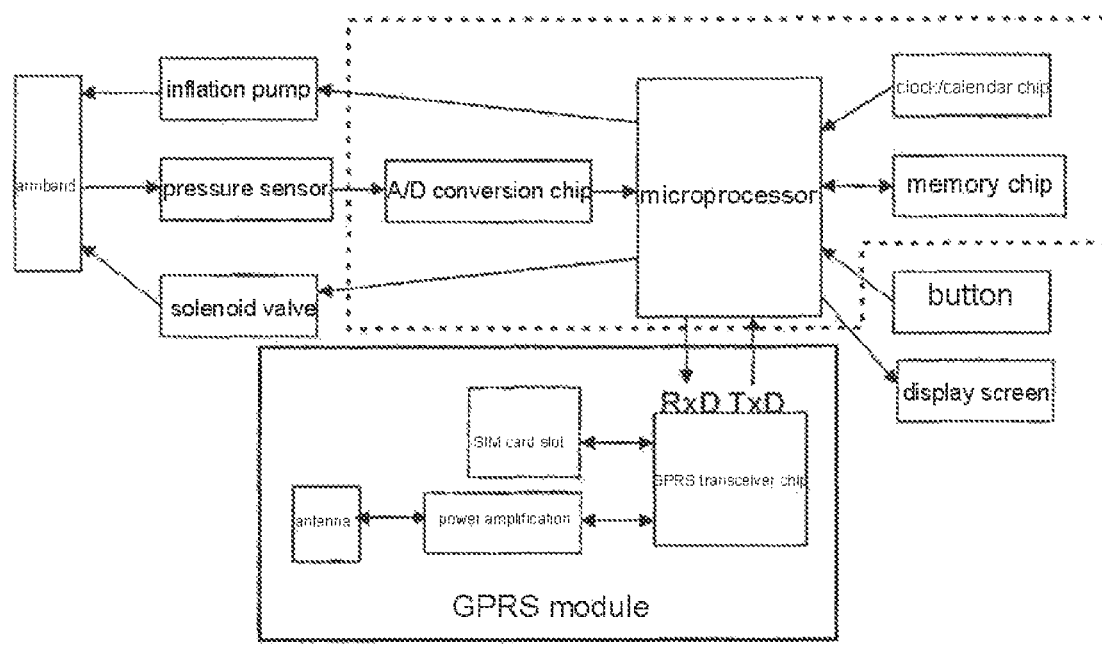
FIG. 3 illustrates a diagram of circuit structure connection inside the ischemic precondition training treatment equipment.

As shown in FIG. 3, the control circuit comprises a microprocessor, an A/D conversion chip, a clock/calendar chip, a memory chip, and a power supply circuit. The microprocessor is further connected to a GPRS module.

Specifically, the GPRS module comprises a GPRS transceiver chip, a SIM card slot, a power amplification chip and an antenna. The GPRS transceiver chip is provided with an RxD port and a TxD port, and is connected with the microprocessor through the RxD port and the TxD port. The GPRS transceiver chip is also connected with the SIM card slot and the power amplification chip, respectively. And, the power amplification chip is connected with the antenna.

The GPRS transceiver chip is provided with the RxD port and the TxD port. The GPRS transceiver chip is connected with a serial communications interface of the microprocessor through the RxD port and the TxD port, reads data from the memory chip, and sends the data back to a background server after the completion of training or blood pressure measurement each time. In order to avoid the loss of transceiving data, the data signals are firstly amplified by the power amplification circuit and then are transmitted and received via an antenna device, and data before the last shutdown is transmitted repeatedly upon each boot-up so as to compare and verify the transceiving data.

The integrated GPRS module enables the measurement, training and failure data to be wirelessly transferred to a server database in real-time. As the clinical effect of precondition training depends on a long-term persistence in training and relies on a long-term data collection, the GPRS module reduces probability of data loss or invalid and thus improves effectiveness and success rate of ischemic precondition training. Furthermore, the doctor can also send information to a patient by means of the GPRS module to guide the patient for a better training and treatment.

The use of the aforesaid ischemic precondition training treatment equipment is for judging health condition of blood vessels.

A method of the aforesaid ischemic precondition training treatment equipment for judging health condition of blood vessels, comprising the following steps:

(1) wearing two armbands on left and right arms of a user respectively, and connecting plugholes of the two armbands with a left armband holder 46 and a right armband holder 47 respectively;

(2) starting the ischemic precondition training treatment equipment, which firstly pressurizes the left arm to begin the first blood pressure measurement, calculates systolic pressure, diastolic pressure and pulse measured from the left arm according to the principle of oscillography, and automatically memorizes and stores the result of the first measurement after the completion of measurement, wherein talking, motion and abnormality of the armbands during the measurement would result in an abnormal measurement result, and the abnormal data would not be memorized, and the measurement would be re-started until an accurate measurement result is obtained;

(3) automatically performing the first blood pressure measurement of the right arm, calculating systolic pressure, diastolic pressure and pulse measured from the left arm, and automatically memorizes and stores the result of the first measurement after the completion of measurement;

(4) after repeating three effective measurements, displaying the difference value of the average value of the systolic pressures and the difference value of the average value of the diastolic pressures measured between the left and right arms on a screen; and (5) judging health condition of blood vessels according to the difference value measured from the step (4).

According to research data, it is generally deemed that the difference value of systolic pressure and the difference value of diastolic pressure between both arms for a normal person shall both be smaller than 10 mmHg. If the upper inter-arm blood pressure difference (IAD) reaches 10 mmHg, the user might have peripheral vascular disease.

In view of the above contents, the present invention not only achieves arbitrary switching of left and right arms to separately perform ischemic precondition training or simultaneous ischemic precondition training of both arms, which meets clinical requirements on ischemic precondition training, but also has a function of judging health condition of blood vessels.

A method for blood pressure measurement by the aforesaid ischemic precondition treatment equipment, comprising the following steps:

(1) when blood pressure of the left arm is measured, firstly an armband is worn on the left arm, a left gas pump 41 starts inflation, a left solenoid valve 44 is opened to inflate a left arm airbag and simultaneously a right solenoid valve 45 closes a right armband gas way; when blood pressure of the user is measured in real-time according to the oscillographic method, a release valve 48 discharges gas uniformly, a left pressure sensor 491 detects a pressure oscillation wave of the gas in the armband in real-time, which pressure oscillation wave is converted into an electrical signal and is filtered, and then a control circuit calculates systolic pressure, diastolic pressure and pulse; after the measurement is completed, the release valve 48 is opened to discharge gas, thereby completing the blood pressure measurement of the left arm;

(2) when blood pressure of the right arm is measured, the left gas pump 41 starts inflation, the right solenoid valve 45 is opened to inflate a right arm airbag, and simultaneously the left solenoid valve 44 closes the left armband gas way; when blood pressure of the user is measured in real-time according to the oscillographic method, the release valve 48 discharges gas uniformly, a right pressure sensor 492 detects a pressure oscillation wave of the gas in the armband in real-time, which pressure oscillation wave is converted into an electrical signal and is filtered, and then a control circuit calculates systolic pressure, diastolic pressure and pulse; after the measurement is completed, the release valve 48 is opened to discharge gas, thereby completing the blood pressure measurement of the right arm.

The mechanism of ischemic precondition training is to stimulate the ability of body tissue cells to resist/tolerate ischemia and to mobilize the ability of the body, organs or tissues to survive and work under oxygen deficit conditions by repeatedly blocking limb blood flow of the upper limb of a patient at intervals, for preventing and treating cardio-cerebrovascular disease, reducing altitude sickness, promoting memory and improving sleep quality. Specifically, a method for performing precondition training by the aforesaid ischemic precondition training treatment equipment comprises the following steps:

(1) when the left arm is subjected to precondition training, the left gas pump 41 and the right gas pump 42 are started simultaneously, the right solenoid valve 45 is closed to block the right arm gas way, and the release valve 48 is closed; the left solenoid valve 44 is opened to rapidly inflate and pressurize the left arm armband airbag, the left pressure sensor 491 detects a pressure signal in real-time and feeds the pressure signal back to the control circuit, and the control circuit closes the left gas pump 41 and the right gas pump 42 simultaneously after the pressure in the armband reaches the set pressure value.

During the process of inflation, the control circuit calculates the time required for reaching the set pressure. If the inflation time of the ischemic precondition training treatment equipment exceeds the time required for reaching the set pressure, the left gas pump 41 and the right gas pump 42 will stop inflation while the release valve 48 will automatically discharge gas to zero pressure, and then the gas pump will be restarted to inflate. During training, when the pressure in the airbag decreases to a low limit value of the ischemic precondition training treatment equipment, the control circuit will start the left gas pump 41 to supplement gas pressure. The left pressure sensor 491 will monitor pressure changes of the gas way during the entire training process, and provide feedback to the control circuit in time so as to make adaptive adjustment. The control circuit controls pressing time, release time and training times correspondingly according to the predetermined program.

(2) When the right arm is subjected to precondition training, the left gas pump 41 and the right gas pump 42 are started simultaneously, the left solenoid valve 44 is closed to block the left arm gas way, and the release valve 48 is closed; the right solenoid valve 45 is opened to rapidly inflate and pressurize the right arm armband airbag, the right pressure sensor 492 detects the pressure signal in real-time and feeds this pressure signal back to the control circuit, and the control circuit closes the left gas pump 41 and the right gas pump 42 simultaneously after the pressure in the armband reaches the set pressure value.

During the process of inflation, the control circuit calculates the time required for reaching the set pressure. If the inflation time of the ischemic precondition treatment equipment exceeds the time required for reaching the set pressure, the left gas pump 41 and the right gas pump 42 will stop inflation while the release valve 48 will automatically discharge gas to zero pressure, and then the gas pump will be restarted to inflate. During training, when the pressure in the airbag decreases to a low limit value of the ischemic precondition training treatment equipment, the control circuit starts the left gas pump 41 to supplement gas pressure. The right pressure sensor 492 will monitor pressure changes of the gas way during the entire training process, and provide feedback to the control circuit in time so as to make adaptive adjustment. The control circuit controls pressing time, release time and training times correspondingly according to the predetermined program.

(3) When both arms are subjected to precondition training simultaneously, the left gas pump 41 and the right gas pump 42 are started simultaneously, the left solenoid valve 44 and the right solenoid valve 45 are opened simultaneously, the release valve 48 is closed, and the gas way is closed. The armband airbags of both arms are rapidly inflated and pressurized, and the control circuit closes the left gas pump 41 and the right gas pump 42 simultaneously when the pressure in the armbands reaches the set pressure value. The armband airbags discharge gas automatically and rest for 3 to 5 minutes after a constant pressure is kept for 3 to 5 minutes and then are inflated and pressurized again. The aforesaid operations are repeated five times, and the precondition training is then completed.

Only preferred embodiments of the present invention are described above. It should be noted that for those ordinary skilled in the art, a plurality of improvements and modifications can also be made without departing from the principle of the present invention, and these improvements and modifications shall also be deemed as falling within the protection scope of the present invention.

The invention claimed is:

1. Ischemic precondition training treatment equipment, comprising a shell, two armbands, buttons mounted on the shell, a display screen and a control circuit, wherein, the shell comprises two armband plugholes for connecting the two armbands on both left and right sides, respectively; the shell also comprising a gas way structure provided within the shell; the gas way structure comprising a 5-way device, which is connected to a left gas pump, a right gas pump, a left solenoid valve, a right solenoid valve and a release valve, respectively;

wherein, the left solenoid valve is connected to a left armband holder, with a left pressure sensor provided therebetween; the right solenoid valve is connected to a right armband holder, with a right pressure sensor provided therebetween; and the left armband holder and the right armband holder are connected with the armband plugholes on both sides of the shell, respectively.

2. The ischemic precondition training treatment equipment according to claim 1, wherein, the control circuit comprises a microprocessor, an Analog/Digital (A/D) conversion chip, a clock/calendar chip, a memory chip, and a power supply circuit, and wherein the microprocessor is further connected to a General Packet Radio Service (GPRS) module.

3. The ischemic precondition training treatment equipment according to claim 2, wherein, the GPRS module comprises a GPRS transceiver chip, a Subscriber Identity Module (SIM) card slot, a power amplification chip and an antenna; wherein the GPRS transceiver chip is provided with a Receive Data (RxD) port and a Transmit Data (TxD) port, and wherein the GPRS transceiver chip is connected with the microprocessor through the RxD port and the TxD port;

wherein the GPRS transceiver chip is also connected with the SIM card slot and the power amplification chip, respectively, and the power amplification chip is connected with the antenna.

* * * * *